| United States Patent [19] | [11] 4,016,038 |
| --- | --- |
| Sugimoto et al. | [45] Apr. 5, 1977 |

[54] PROCESS FOR PREPARING MALTOSES FROM STARCHES

[75] Inventors: Kaname Sugimoto; Mamoru Hirao; Masashi Kurimoto; Eikichi Miyake, all of Okayama, Japan

[73] Assignee: Hayashibara Company, Okayama, Japan

[22] Filed: Mar. 27, 1972

[21] Appl. No.: 238,608

Related U.S. Application Data

[63] Continuation-in-part of Ser. No. 810,359, March 25, 1969, abandoned.

[30] Foreign Application Priority Data

Apr. 1, 1968 Japan .............................. 43-21367

[52] U.S. Cl. ............................ 195/31 R; 195/66 R
[51] Int. Cl.² ...................................... C12D 13/02
[58] Field of Search .............................. 195/31, 66

[56] References Cited

UNITED STATES PATENTS 3,565,765 2/1971 Heady et al. .................... 195/31 R
3,708,396 1/1973 Mitsuhashi et al. ............. 195/31 R

FOREIGN PATENTS OR APPLICATIONS 2,005,304 12/1969 Germany

*Primary Examiner*—Raymond N. Jones
*Assistant Examiner*—T. G. Wiseman
*Attorney, Agent, or Firm*—Browdy and Neimark

[57] ABSTRACT

This invention has made it possible to uniformly gelatinize and disperse a highly concentrated starch slurry of a concentration as high as 10% or more by gelatinizing at an elevated temperature; hitherto it was considered next to impossible to uniformly gelatinize and disperse such highly concentrated starch slurries, and, according to the present invention, the upper limit of saccharification of the starch slurry is increased by selectively decomposing the $\alpha$-1,6-glucoside bonds in the starch by means of an $\alpha$-1,6-glucosidase and, thereby, to make it possible to obtain a highly pure maltose.

2 Claims, No Drawings

PROCESS FOR PREPARING MALTOSES FROM STARCHES

This application is a continuation-in-part of co-pending U.S. Application Ser. No. 810,359 filed Mar. 25, 1969 now abandoned.

This invention relates to a process for economically preparing highly pure maltoses at high concentrations from various starch slurries at 10% or higher concentrations, which comprises gelatinizing such a slurry evenly at an elevated temperature of not lower than 100° C., and then rapidly cooling the gelatinized solution and, at the same time, subjecting it to the action of any of various $\alpha$-1,6-glucosidases and $\beta$-amylase.

More particularly, this invention concerns a novel process for preparing maltoses as already disclosed by the same applicant in the co-pending application (U.S. patent application Ser. No. 735,988 filed June 11, 1968 now abandoned in favor of continuation application Ser. No. 177,829 filed Sept. 3, 1971 now U.S. Pat. No. 3,795,584.) entitled "Process for Preparing High-Purity Maltoses", which consists of liquefying or gelatinizing a starch slurry and then subjecting the liquefied or gelatinized starch to the action of an $\alpha$-1,6-glucosidase and $\beta$-amylase to yield a high purity maltose. The process is aimed, first of all, at treating amylopectin, the major constituent of starch and which has a branched structure, with one of various $\alpha$-1,6-glucosidases thereby selectively hydrolyzing the branching parts of the branched structure to form straight-chain molecules such as of amylose which are completely decomposable with $\beta$-amylase. Here it should be noted that it has hitherto been impossible to decompose the amylopectin having a branched structure completely with $\beta$-amylase. Although $\beta$-amylase decomposes amylopectin gradually up to the branching parts, it cannot decompose the structure of the branching bonds, or $\alpha$-1,6-glucoside bonds, and thus leaves so-called $\beta$-limit dextrin behind.

Therefore, the present invention has an important significance in that it is directed to the decomposition of the branching bonds with an $\alpha$-1,6-glucosidase for the elimination of the above-said obstacle beforehand so that the starch can be completely decomposed into maltose.

The second aim is that, even when the starch has beem completely decomposed by the $\alpha$-1,6-glucosidase into amylose type molecules of straight-chain bonds, the amylose molecules with an odd degree of polymerization leave glucose or maltotriose eventually by $\beta$-amylolysis and thus, when the amylose molecules to be subjected to the $\beta$-amylolysis are of a low molecular weight, the production of maltose by the $\beta$-amylolysis should be low.

This means that the decomposition of starch for the purposes of liquefaction or gelatinization must be carried out to a minimum degree only enough to maintain it in liquid form. For these reasons, it is desirable to use a starch slurry of the lowest possible concentration and simply gelatinize it in the vicinity of neutrality rather than liquefy it with $\alpha$-amylase or an acid.

However, uniform gelatinization of starch at a concentration as high as 10% or more is next to impossible from the industrial viewpoint. In commercial production, therefore, a process has to be resorted to in which considerations are given to the concentration and purity of the maltose to be produced.

With the view to achieving improvements in those respects above described, the present invention provides a process for liquefying a highly concentrated starch slurry at an elevated temperature. In the previously disclosed process of U.S. patent application Ser. No. 735,988 filed June 11, 1968 now Ser. No. 177,829 filed Sept. 3, 1971, a starch slurry is heated and dispersed at 100° C. and is then further heated at 130° C. for complete dispersion or, with the addition of $\alpha$-amylase, it is decomposed at a low rate of decomposition at about 90° C. However, the concentration before the reaction with an $\alpha$-1,6-glucosidase is suitably not higher than 10%, and this is too thin for commercial operation. In the course of the development of the present invention diversified tests were conducted at gelatinization temperatures of upwards of 100° C. in order to obtain a uniformly dispersed, high-molecular decomposed solution (gelatinized, dissolved solution). The liquefaction with a $\alpha$-amylase is not suitable for the liquefaction and dispersion of corn starch or wheat starch, and because the secondary product of small molecules can not be avoided. Then the heating and dispersion of the starch near the neutrality were studied.

The present inventors used corn starch which usually resists complete gelatinization, heated in at concentrations of over 20% in an autoclave with stirring, and observed the dispersed state at different temperatures. They found, as the result, that the hydrolysis of the starch takes place to considerable degrees and the viscosity drops and, with the elapse of time, the reducing power is greatly increased, and further that, at temperatures above 170° C., the decomposition of dextrose itself proceeds appreciably. Thus, they found that a uniformly liquefied product is obtained by treating the starch in such a way as to ensure uniform heating at temperatures up at 170° C. Since the gelatinization and dispersion at high concentrations involve a rapid increase in viscosity in the early stage of heating, a continuously operable apparatus having a powerful agitation means is desirable. With this in view, the continuous equipment of direct steam heating type described in the published specification of Japanese Pat. No. 426,978 was employed for the experiments. It has thus been found that a mash concentration of not more than 40% and a temperature of not higher than 170° C., preferably 150° to 160° C., gave good results, Under these conditions and with a retention time of 10 to 30 minutes, a viscous, homogeneously dispersed matter with a decomposition rate of not more than D.E. 1% was obtained. Similar results are given by a rotary heat exchanger of indirect heating type. In the latter case, no dilution due to steam draining is involved and therefore an initial mash concentration of not more than 35% is desirable.

The gelatinized starch solution thus prepared is a clear, viscous and homogeneous dispersion. With a drop of the temperature it will become white and retrograde unsuitably for the enzymatic reaction. It is advisable, for this reason, to cool the gelatinized solution rapidly and uniformly and mix it thoroughly with the enzyme before retrogradation can occur and thus cause the decomposition and dilute it rapidly by pouring and dispersing it with stirring into a large amount of a saccharified solution which is decreased in viscosity with a fairly high degree of saccharification. Considering the heat resistance of the enzyme, it is beneficial to cool it to 60° to 70° C., admix $\beta$-amylase, and decrease the temperature to 45° C. while the saccharification is in progress, and pour it into a mash tank with agitation while admixing an α-1,6-glucosidase. An example of equipment suitable for this purpose is of such construction that a gelatinized starch solution is sprayed into a vacuum cooler and while its pressure is kept under control and the temperature is maintained in the range of 60° to 70° C., a β-amylase solution at 60° C. is also sprayed in the same cooler by means of a metering pump, and thus the two solutions are thoroughly mixed in the form of minute droplets. In this way cooling and mixing are accomplished almost instantaneously. The resulting solution is cooled to 45° C. and, while the pH is being suitably adjusted, α-1,6-glucosidase is added and mixed through a mixer and poured into the mash tank with stirring. Thus, from the high-molecular and low-decomposition-rate gelatinized starch solutions prepared in the manner above described with high concentrations, it has become possible to produce maltoses of higher purity than conventional products, as illustrated by the following examples.

into a mash tank with agitation and was reacted there at 45° C. for 48 hours. The results were as tabled below.

| | | | | | | | | | |
|---|---|---|---|---|---|---|---|---|---|
| Mash conc. before sacharifn. (%) | 10.0 (10.0) | 11.5 | 13.0 | 13.7 | 14.5 | 16.1 | 19.9 (20.0) | 23.1 | 30.0 |
| Conversion coef. (.D.E.) | 62.2 (61.5) | 62.0 | 61.8 | 62.0 | 60.8 | 60.2 | 60.2 (58.2) | 60.2 | 60.2 |
| Saccharide composition | | | | | | | | | |
| Glucose (%) | 0.5 (1.0) | 0.5 | 0.8 | 1.0 | 0.9 | 1.1 | 0.9 (1.5) | 0.6 | 0.5 |
| Maltose (%) | 95.1 (93.0) | 94.7 | 94.5 | 93.1 | 92.5 | 91.3 | 90.8 (86.8) | 90.0 | 91.0 |
| Maltriose (%) | 2.4 (4.5) | 3.3 | 3.0 | 4.3 | 4.7 | 4.8 | 5.2 (7.0) | 5.0 | 5.0 |
| Higher saccharides (%) | 2.0 (1.5) | 1.5 | 1.7 | 1.6 | 1.9 | 2.8 | 3.1 (4.7) | 4.4 | 4.5 |

The saccharide composition was estimated on separation by paper chromatography. Values in parentheses represent the results of corresponding tests conducted in accordance with the process of U.S. application Ser. No. 735,988 filed previously and assigned to the same assignee as the present application.

As can be seen from the results above tabulated, the high-temperature liquefaction and high-concentration saccharification according to the present invention signify a remarkable technical progress over the previous process proposed by applicant. The present process permits saccharification with a concentration more than twice that for the preceding process, and also enhances the decomposition limit (or maltose purity). Since maltose is hard to obtain with a high purity, the present process which makes it possible to get over 90% pure products directly represents a great improvement from the industrial standpoint. Further, in view of the fact that, where a 100% pure product is to be manufactured, the difference of only a few percent in purity in the neighborhood of 90% can have a material influence upon subsequent recrystallization, the present invention has a very important significance and extreme practical advantages.

EXAMPLE 1

Purified corn starch was adjusted to pH 5 to 6 and a concentration of 15 to 35%. Using a continuous starch liquefying equipment (as described in the published specification of Japanese Pat. No. 426,978, it was forced into a multi-blade heating-agitating column through a metering pump. Also live steam was fed into the bottom of the column and the temperature inside the column was automatically adjusted to the range of 160° to 165° C., while the flow rate was so controlled as to provide a retention time of 15 minutes. The decomposition rate of the gelatinized solution thus attained was about 0.5 to 1% D.E. While varying the concentration of the starch charged, the concentration of the gelatinized solution was determined, and β-amylase was used at a rate of 100 units per gram of the starch. The gelatinized solution was sprayed into a vacuum cooler through an upper nozzle and, at the same time, β-amylase was introduced therein at the rate above specified through an enzyme-spraying nozzle on the upper part of the cooler. While the liquefied starch solution was kept under automatic temperature control at 65° c., the two were mixed together. From the lower part of the cooler the mixed solution was continuously drained and cooled by a heat exchanger to 45° to 50° C., and immediately, with the aid of an agitator, an α-1,6-glucosidase (e.g., the one already described in U.S. Pat. No. 3,560,345 and U.S. Pat. No. 3,622,460 was forced therein at a rate of 20 units per gram of the starch by a proportional pump. The pH of the mixture was adjusted to 5.7 to 6.0, and it was immediately fed

EXAMPLE 2

A gelatinized starch solution prepared by treating purified corn starch in the same way as described in Example 1 was decomposed with α-1,6-glucosidase produced by *Lactobacillus plantarum*. This enzyme is a new discovery which is more resistant to heat than the similar enzyme originating from the genus Aerobacter, withstanding the heat of 55° C. or higher temperatures. It also exhibits an optimum reaction temperature of upwards of 50° C. This enzyme was added to the gelatinized solution in the following manner. The solution kept at over 150° C. was sprayed into a vacuum cooler from the upper part thereof and cooled to 50° to 56° C. Meanwhile, the Lactobacillus enzyme solution warmed to 45° C. was sprayed from the upper part of the vacuum cooler at a rate of 30 to 20 units per gram of the starch. The pH of the mixed solution was adjusted to 6 to 7. While the solution was cooled to 45° to 50° C., it was thoroughly mixed with β-amylase which was introduced at a rate of 100 units per gram of the starch.

An attempt was made in this example to premix the β-amylase with the Lactobacillus enzyme and add the mixture to the gelatinized starch solution. The result so obtained was not different from the above result.

The reactant solution was kept at 45° to 50° C. for 48 hours. On completion of the reaction, it was heated, decolored in the usual manner, and purified by ion exchange, and then concentrated and crystallized with a 10% water content. Analysis by paper chromatography showed no significant distinction between the saccharide composition thus obtained and that which resulted in Example 1. Thus, from reactant solutions with concentrations of over 20%, high-purity, colorless products having 90% or higher maltose contents were obtained.

of the starch. Each of the resulting mixtures was reacted at 50° to 55° C. for 40 hours, each enzyme added was deactivated by heat. Colorless maltose solution was obtained in each case by passing the aforesaid reaction product solution through a decoloring activated carbon and an ion exchange apparatus. The resulting colorless maltose solution was concentrated to 90% of concentration and it was allowed to stand until crystallization of the maltose occurred. Colorless and sublimated product maltose of 90% yield was obtained. Each product maltose was chromatographically fractionated and determined and the results are shown in the following Table.

| Enzyme sources of alpha-1,6-glucosidase | | Lactobacillus brevis IFO 3345 | Lactobacillus brevis IFO 3960 | Lactobacillus bulgaricus IFO 3533 | Lactobacillus gayonii ATCC 8289 | Lactobacillus plantarum ATCC 8008 |
|---|---|---|---|---|---|---|
| Concentration of starch emulsion | | 20 | 25 | 25 | 23 | 23 |
| D.E. of saccharified solution | | 62.1 | 60.1 | 60.0 | 61.0 | 60.2 |
| Sugar components of the product | glucose | 0.5 | 0.6 | 0.6 | 0.5 | 0.6 |
| | maltose | 91.5 | 90.3 | 90.0 | 91.0 | 90.0 |
| | maltotriose | 5.0 | 4.2 | 4.3 | 4.1 | 5.0 |
| | oligosaccharides | 3.0 | 4.9 | 5.1 | 4.4 | 4.4 |

EXAMPLE 3

Purified starch was adjusted to a concentration of 15 to 35% thereby to obtain a starch emulsion, then the pH of the emulsion was adjusted. The emulsion was forced into a continuous multi-blade agitating tank in which the temperature inside the tank was adjusted to 150° to 165° C. by the feed of steam to liquefy the starch emulsion. The decomposition rate of liquefied solution was below 1 D.E. The liquefied solution was sprayed into a tank with a normal pressure and cooled to 100° C. Then the resulting mixture was sprayed into a vacuum tank and cooled to 55°–65° C., while β-amylase at a rate of 70 units per gram of the starch was introduced therein, and then the mixture was quickly mixed together. The resulting solution with a reduced viscosity was withdrawn from the lower part of the tank and cooled to 55° C., while the pH of the cooled solution was adjusted to 7.0. Thereafter it was divided into five equal parts, and to each of them one of five kinds of enzymes prepared from their corresponding genus of Lactobacillus was added at a rate of 30 units per gram of the starch.

What is claimed is:

1. A process for directly preparing maltose of high purity from starches which comprises uniformly gelatinizing and dispersing a starch slurry with a concentration of not less than 10% by weight at an elevated temperature of between 150°–170° C,; rapidly cooling the resulting dispersed starch solution to a temperature between 40° to 70° C. before retrogradation can take place; then adding a heat resistant alpha-1,6-glucosidase produced from *Lactobacillus plantarum* and β-amylase thereto; and conducting a saccharification of the mixture.

2. A process for preparing maltose in accordance with claim 1 wherein said cooling step and said adding step are accomplished by rapidly cooling the dispersed starch solution to a temperature between 50° and 60° C. and then adding said heat resistant α-1,6-glucosidase, and further cooling the solution to a temperature between 40° and 50° C. and then adding the β-amylase thereto.

* * * * *